(12) United States Patent
Libasci

(10) Patent No.: US 9,506,851 B2
(45) Date of Patent: Nov. 29, 2016

(54) PARTICLE SIZE CLASSIFICATION DEVICE FOR FIELD USE

(71) Applicant: Linda Libasci, College Station, TX (US)

(72) Inventor: Linda Libasci, College Station, TX (US)

( * ) Notice: Subject to any disclaimer, the term of this patent is extended or adjusted under 35 U.S.C. 154(b) by 0 days.

(21) Appl. No.: 14/872,241

(22) Filed: Oct. 1, 2015

(65) Prior Publication Data

US 2016/0047729 A1 Feb. 18, 2016

Related U.S. Application Data

(63) Continuation-in-part of application No. 29/498,415, filed on Aug. 4, 2014, now Pat. No. Des. 743,461.

(51) Int. Cl.
*G01F 19/00* (2006.01)
*G01D 11/24* (2006.01)
*G01N 15/02* (2006.01)

(52) U.S. Cl.
CPC ........... *G01N 15/0272* (2013.01); *G01F 19/00* (2013.01)

(58) Field of Classification Search
CPC ................................ G01D 11/24; G01F 19/00
USPC .................................................. 73/426, 427
See application file for complete search history.

(56) References Cited

U.S. PATENT DOCUMENTS

| | | | | |
|---|---|---|---|---|
| 2,326,762 A * | 8/1943 | Collier | ...................... | B07B 1/02 209/357 |
| 3,120,323 A * | 2/1964 | Sparling | .............. | B65D 21/048 206/505 |
| 4,534,858 A * | 8/1985 | Aldrich | .................... | A47J 43/22 209/236 |
| 5,137,316 A * | 8/1992 | Foos | ..................... | G01F 19/002 206/520 |
| 7,077,054 B1 * | 7/2006 | Hurlock | .............. | A47J 31/0636 210/465 |
| 7,753,206 B2 * | 7/2010 | Sawhney | ................ | G01F 19/00 206/514 |
| 8,678,198 B1 * | 3/2014 | D'Andrea | ............. | G01F 19/007 209/417 |
| 2005/0172819 A1 * | 8/2005 | Chen | ................... | A47J 31/4496 99/279 |
| 2008/0099382 A1 * | 5/2008 | Shih | ....................... | B01D 35/06 210/85 |
| 2009/0044622 A1 * | 2/2009 | Barber | .................... | G01F 19/00 73/426 |
| 2014/0134304 A1 * | 5/2014 | Picozza | ............... | A47J 43/0716 426/231 |

FOREIGN PATENT DOCUMENTS

| | | | |
|---|---|---|---|
| CN | 202057377 U | * | 11/2011 |
| CN | 202173301 U | * | 3/2012 |
| CN | 202387010 U | * | 8/2012 |
| CN | 203106595 U | * | 8/2013 |
| CN | 203354237 U | * | 12/2013 |

* cited by examiner

*Primary Examiner* — Lisa Caputo
*Assistant Examiner* — Jamel Williams
(74) *Attorney, Agent, or Firm* — Douglas Baldwin

(57) ABSTRACT

Disclosed is a size portable particle size distribution sampling device that is small enough to be carried by truckers and handled by terminal personnel. The device consists of multiple nesting screening (sieve) cups, with a sample cup at the top, a plurality of screening cups in sequence below the sample cup and a base container at the bottom. Methods of use are also disclosed.

10 Claims, 5 Drawing Sheets

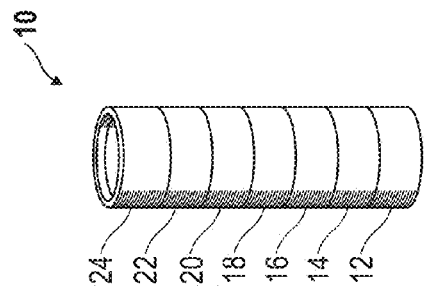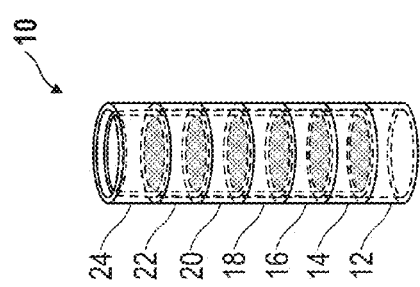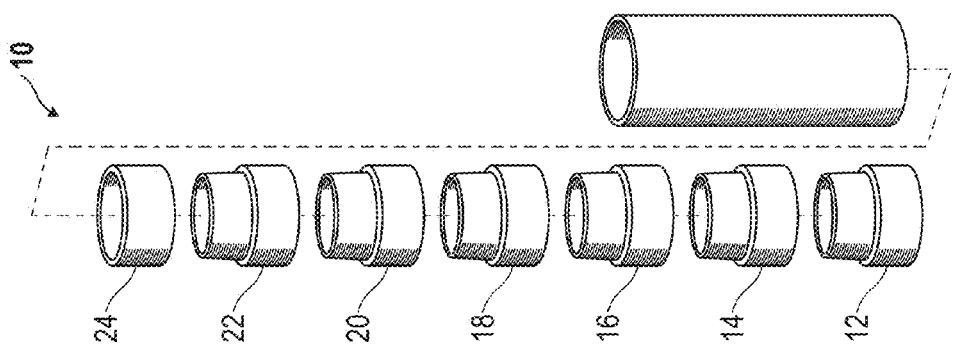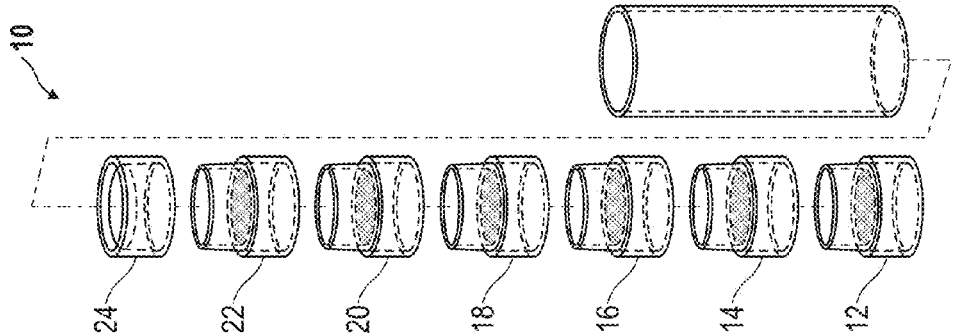

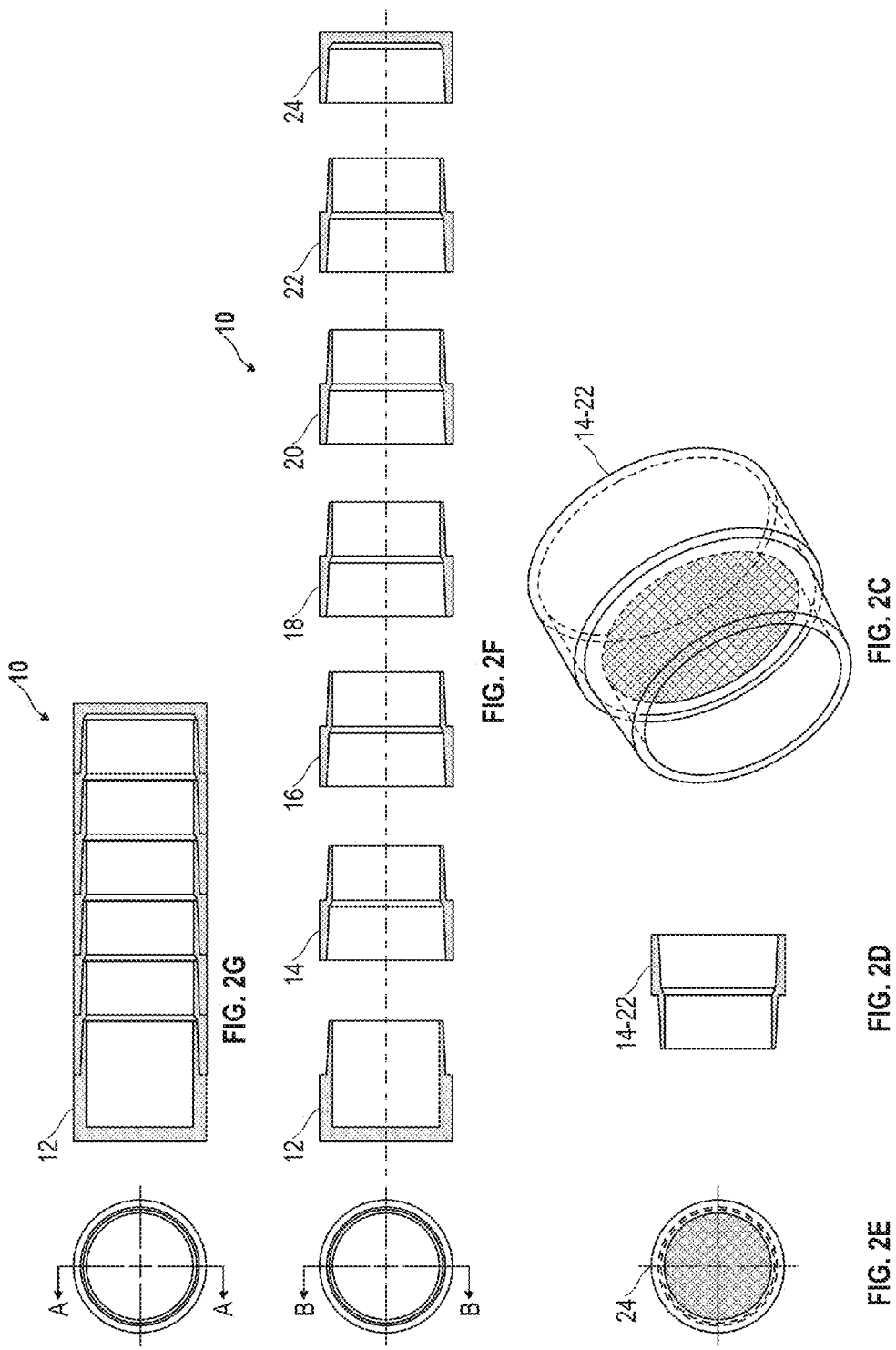

PARTICLE SIZE CLASSIFICATION DEVICE FOR FIELD USE

CROSS REFERENCE TO RELATED APPLICATIONS

The present application is a continuation-in-part application of Ser. No. 29/498,415, filed Aug. 4, 2014, the disclosures of which is hereby incorporated by reference in its entirety for all purposes.

BACKGROUND

Field of Invention

This disclosure is in the field of devices for classification of particle size distribution and specifically those particularly suited for classification of sand particles.

Background

There is a need for a portable particle size classification device and system. It has been said "By far the most important physical property of particulate samples is particle size. Measurement of particle size distributions is routinely carried out across a wide range of industries and is often a critical parameter in the manufacture of many products. The particle size distribution has a direct influence on material properties . . . ".www.Malvern.com/ParticleSize. While such a classification devices are useful in many areas they can be particularly useful in determining particle size distribution for sand used as proppants in hydrofacturing (fracing) operations in oil and gas well drilling. Sand particles are used in hydrofracturing operations as a means to help hold open fractures generated by high pressure water injection—they prop up the cracks, thus "proppants". While there are numerous particulate materials proposed for such use, sand is most commonly used because of its availability and relatively low cost. However, sizing is often critical and there is a need for an inexpensive portable means of ensuring that what is delivered to a drill site is what has been ordered. The present invention is such a device.

BRIEF DESCRIPTION OF FIGURES

FIG. 1A is a side view of an embodiment of the invention.
FIG. 1B is a side view of an embodiment of the invention.
FIGS. 2A-2G are views of expanded view of the components of an embodiment of the invention.

DETAILED DESCRIPTION

Today, trucks and railcars are loaded and unloaded with hydro-fracturing (frac) sand without the terminal operators, truck drivers or service company personnel ever testing and verifying the type of sand they are handling. There are significant liability risks in not confirming the sand identification, product, or particle size distribution before pumping it down a well. This can lead to a multimillion dollar claim from the exploration and production company against its contracted hydraulic fracturing service provider for the removal of the non-specified material or underperformance of the well. What the industry needs is a quick and cost effective way to confirm the particle size distribution (and thus the product) of the sand being handled by the terminals and operators at the well site.

The device of this invention is useful to classify particle size distribution of particles and is especially useful for classification of samples of sand such as hydraulic fracturing (fracing) proppant sand. By using the device of the invention, sand classification can be accomplished in 30 seconds or less. While the device will not replace or perform standard ISO/API sieve test, it is a convenient, fast and low cost means to check particle size distribution in the field. It also serves as a container for the retention of a sand sample for quality control purposes.

There are, typically, five sieve sizes that allow a rapid assessment of the size distribution of the most common frac sands pumped in North America: 16/30, 20/40, 30/50, 40/70 and 100 Mesh. The traditional ISO/API/ASTM sieve test requires thousands of dollars of equipment and takes about 10 minutes per sample. There are many rules in the ISO/API/ASTM test for ensuring a proper sample is used. These same rules make it impractical for use in the field. It is impractical at most field locations outside the originating mine from where it comes.

The device of embodiments of the present invention provides most of the benefits of the traditional sieve test and cut the test time down to 30 seconds or less. A truck driver delivering sand can collect a sample when he goes to close the hatch on his trailer; the test can be conducted by the driver before driving away from the terminal. This equates to no loss of time in truck loading. Terminal railcar unloading crew can take a sample to confirm the product in a railcar before unloading.

Figure 3D:
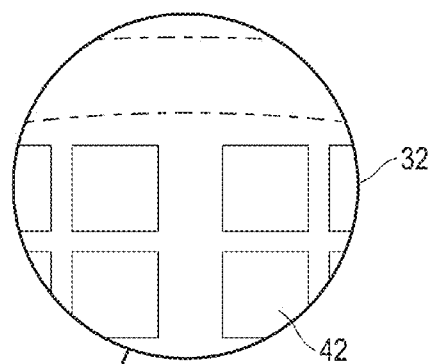
FIGS. 3A-3D are drawings of sections of typical screen cups of an embodiment of the invention.
Figure 3A:
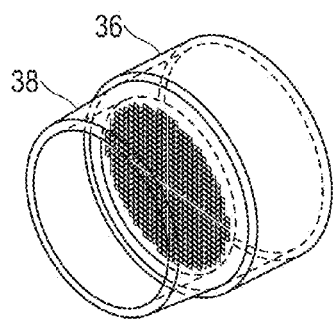
Figure 3C:
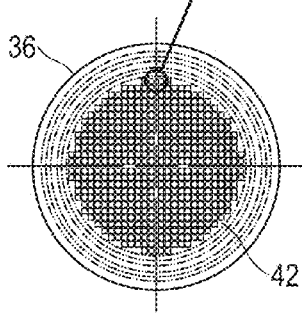
Figure 3B:
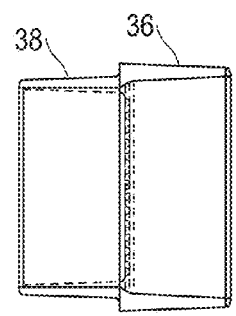
Figure 4B:
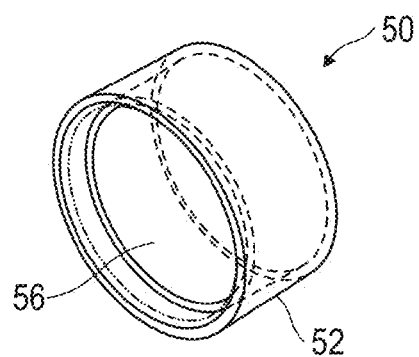
FIGS. 4A-4C are drawings of sections of a typical base cup of an embodiment of the invention.
Figure 4C:
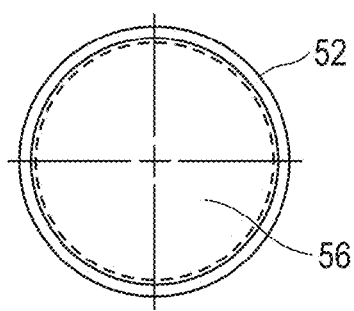
Figure 4A:
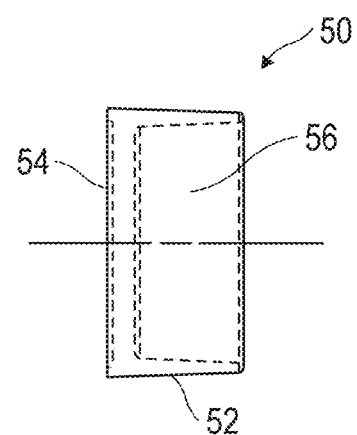
Figure 5A:
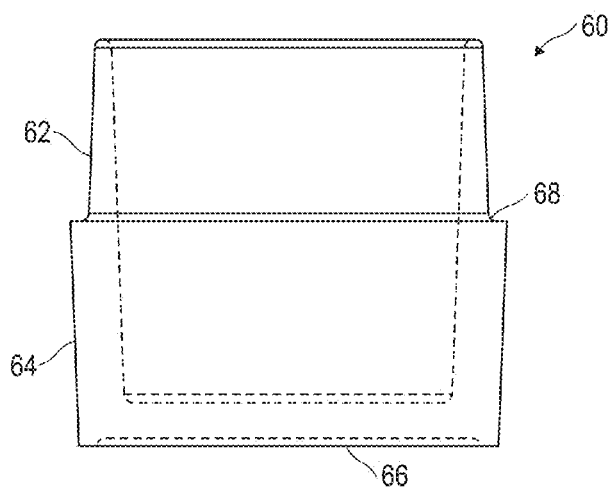
FIGS. 5A-5D are drawings of sections of a typical top measuring cup of an embodiment of the invention
Figure 5B:
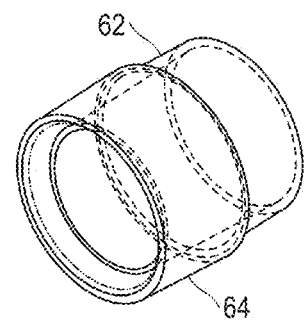
Figure 5D:
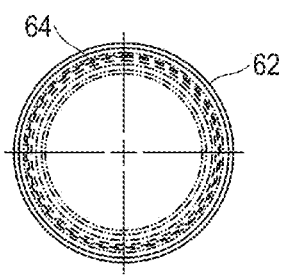
Figure 5C:
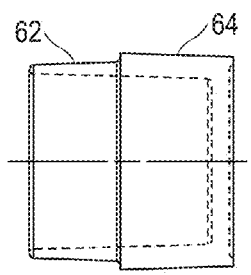

In one embodiment the device of the invention comprises a sample container that is about the smallest container that can handle a useful sand sample size. It is small enough to be carried by truckers and handled by terminal personnel. A sample size is approx. ½ ounce or 18 grams is sufficient. The device consists of multiple nesting screening (sieve) cups, with a sample cup at the top, a plurality of screening cups in sequence below the sample cup and a base container at the bottom. Referring to the Figures, FIGS. 1A and 1B are views of an assembled prototype of an embodiment of the device of the invention, 10. Item 12 is the top measuring cup, followed by stacking screening cups 12-22. FIGS. 2A to 2H show expanded views of the prototype, FIG. 2A shows the components, FIG. 2B the components with screens, FIG. 2C is a perspective view of a screen cup and FIGS. 2D-2H show other details. The cups are stacked by having a bottom section of the cup smaller than the interior of the next cup top section so that they fit together at with final joints 15-23. They are nesting or interlocking in that the small outside section of one cup fits snugly into the inside of the larger section of the next following cup as can be seen in FIGS. 2A-2G. The cups are shaped as shown in FIGS. 2A, 2B, 2C, 2D, 2F, 3A, 3B, 4B, 5A and 5B and 5C. FIGS. 2A-2G are views of the bottom the sections or components of a prototype device. A typical screen cup is illustrated in FIGS. 2C-2D and 3A-3D. As shown, each cup has an enlarged cup section 36 and a smaller diameter section 38. Section 38 will fit into the inside of a cup below it in the top section as 36. Between sections 36 and 38 is a screen that is placed perpendicular to the length of the cup. FIGS. 3C, 3D shows the screen section 32 with screen holes 42. Each of the cups, 14-22, in FIGS. 1 and 2 will be shaped in this way but with different screen holes or mesh sizes. FIG. 4A-4C illustrates a base, 50, for the device. It has open space 54, walls 52 and a bottom 54. It is designed so that a screen cup bottom section will fit into the top inside of 56. FIGS. 5A-5D illustrates a measuring cup, 60, that fits at the top of the device. Cup 60 has a small section 62 and a large section 64 and bottom 66. Sand or other material that is to be screened is placed in the cup to the indicated fill line 68 with small section 62 upright. The cup is then attached to the stacked screen cups and inverted so that the material flows downward through the sequenced screens in the screen cups. The relative amounts of particles in each screening cup can be estimated visually or the cups dissembled (un-stacked) and the amount of particles in each cup measured. In one embodiment, there are marking or scorings on the circumference of the screening cups to aid in estimating the relative amount of particles.

As illustrated, the individual screen cups are separate and detachable. However, they may be permanently connected (so that the interlocking sections are not required) with only the base and top measuring cups detachable.

The device is preferably made of plastic (polymer) material but may be made of any suitable material including various polymer materials, glass or metals. It is preferred that the material be sufficiently transparent that particles may be seem through the walls by normal eyesight. If opaque materials are used it is desirable to provide transparent windows. A prototype was made of transparent polystyrene crystal.

Since the device is particularly useful for field use it should be small enough to be easily carried into the field. It is very suitable to have cups of less than about three (3) inch diameter and with the top larger section less than about two (2) inches in length. A prototype has cups of 2⅓ inch diameter and height (of larger section) of about one inch.

Sampling and Frac Proppant Sand Specifications

Sand or other material to be classified should preferably be flowing when sampled. Multiple samples should be collected, combined and then split into the final test sample. The only organizations that currently implement these practices are the sand mines and they accomplish these steps with expensive automated sampling equipment. The remainder of the industry needs a quick and effective tool.

According to the API/ISO/ASTM standard sieve test, 90% of the particles in a sand sample should fall between the two sieve sizes that designate the material grade:
16/30—90% of the sand particles should be trapped between 16 and 30 mesh sieves
20/40—90% of the sand particles should be trapped between 20 and 30 mesh sieves
30/50—90% of the sand particles should be trapped between 30 and 50 mesh sieves
40/70—90% of the sand particles should be trapped between 40 and 70 mesh sieves
100 Mesh—100% of the material should pass through a 100 mesh sieve Product segregation is a huge issue for sand suppliers. Top tier producers go to extremes to ensure the product quality with the proper particulate size distribution. Railcars have many samples taken from the 100 ton flow of product into the car. Each car is tested to the ISO standard and upstream production is constantly adjusting the process to ensure the material passes the standard test. However, the sand particles are constantly seeking to undo all the hard work at the mine due to transportation vibration and handling at the terminal, in the truck and at the well site. The fines gravitate to the bottom of the pile—leaving coarser grains at the top. The sand received is not necessarily the sand that was loaded at the mine. It is difficult to hold to 90% within specification at the destination.

The desired standard to employ with the an embodiment of the invention for frac proppant sand is that most of the sand particles should fall between the two sieves designated by arrows, 11 and 13 in FIG. 1, on the side of the device in order to identify the sand type.

A prototype was designed to rapidly identify frac sand by it basic particle size distribution. It was designed to be, in some embodiments, disposable. The finest mesh in the prototype is 70 mesh. So, an assumption is made that anything passing through all five screen cups is 100 Mesh. Screen sizes 80, 90 and 100 mesh sieves were not include in the prototype order to keep the unit small, quick to use and affordable. They could easily be added.

The device may be checked for accuracy before use in a number of ways. For example, 1.) procure standard samples of each mesh in the US and compare to the sieves in the device upon arrival to determine if they are in the proper order; 2.) compare the mesh size under a high power magnifier; 3.) use needles of certain size and see how far they penetrate down the sieve stack?

ISO/API/ASTM Sieve Testing Standards

The following are current standards ISO 13503 for particles size determination. ASTM E11 is the standard with 80-120 gram sample. All samples should be obtained from a flowing stream of proppant. Samples shall not be taken from a static pile. The sampling device should be used with its length perpendicular or the flowing proppant stream, passing at a uniform rate from side to side through the full stream width of moving proppant. This needs to be done as the material is moving to or from a conveyor belt into a blender, truck or railcar. Two metric tons need to flow prior to taking the first sample. During sampling, the device will be passed completely across the moving stream in a brief interval of time. Under no circumstance should the device overflow. If flowing material isn't possible, a combined bulk sample of proppant (or an entire sack up to 50 kg) can be used. Using a sample splitter, obtain $\frac{1}{16}^{th}$ of the sample and test that. Sufficient proppant must be available to split.

Use 9 samples per railcar; 3 per truck are required. Samples must be combined and tested; 5 per 100,000. Allow material to flow for two minutes. Calibrated sieves complying with ASTM E 11-95 Specifications for wire-cloth sieves for testing purposes.

Examples of a Prototype Specification for a Device of the Invention.

| Chart for Mesh Sizes used in a Prototype Device | | |
|---|---|---|
| Mesh Size | Nominal Opening (inches) | Nominal Opening (microns) |
| 20 | 0.033 | 850 |
| 30 | 0.024 | 600 |
| 40 | 0.017 | 425 |
| 50 | 0.011 | 300 |
| 70 | 0.008 | 212 |

The device is useful to highlight that a sand sample can meet the specifications of two sand grades at one time. A sample can appear to meet the specifications for 20/40 and 30/50 at the same time; it can meet the specifications for 30/50 and 40/70 at the same time.

A sample in a prototype device was shipped as 40/70 by a major sand producer. Most of the material falls between the 40 and 50 mesh sieves with approximately 10% or more passing through the 70 mesh into the bottom chamber. Since we know the material was shipped as 40/70, then we can confirm its identification as 40/70. If we did not know in advance that it was 40/70, then there would be a question as to whether it is a "High Cut" or coarse 40/70 or a rather fine grade of 30/50.

The device of the invention has been generally described in an embodiment for classifying frac sand but it will be realized it may be adapted for use in classifying any sample of particles and while it has been described in connection with one or more exemplary embodiments, it is not intended to limit the claims to the particular forms set forth. For example, it is useful in ad can be adapted for classifying sand for glass making and other related applications. The exemplary screen sizes are likewise only exemplary and may be adapted and changed to accommodate the particular participles to be classified. The appended claims are intended to cover such alternatives, modifications and equivalents as may be included within their spirit and scope.

The invention claimed is:

1. A particle size measuring device comprising a measuring cup, a base cup and a plurality of screening cups that are structured to nest together with a bottom section diameter smaller than the inside diameter of the next succeeding cup in a nest and wherein no more than about half of the side walls of each cup is overlapping with another nested cup when the cups are nested and, wherein the screening cups have disposed in each cup a fixed screen of predetermined mesh size.

2. The device of claim 1 wherein are screening cups having a screen size of 20, 30, 40, 50 and 70 mesh.

3. The device of claim 1 wherein the measuring cup, the base cup and screening cup(s) of the device are made of material sufficiently transparent for particles to be seen through the walls or if opaque have viewing windows.

4. The device of claim 1 wherein the measuring cup, the base cup and screening cup(s) all have diameters less than about three inches and a height of less than about two inches.

5. The devise of claim 1 wherein the screening cup or cups have marking to allow determination of the height of its content.

6. A method of field testing the size distribution of a sample of particles comprising; taking a representative sample of particles:
 placing the sample in a measuring cup structured to nest with a series of nested screening cups wherein each screening cups have fixed screens in each and wherein the bottom section diameter of each is smaller than the inside diameter of the next succeeding cup in a nest and wherein no more than about half of the side walls of each cup is overlapping with another nested cup when the cups are nested together and;
 placing the measuring cup into a device comprising a measuring cup, a base cup and a plurality of screening cups that are structured to nest together, wherein each screening cup has disposed in each a screen of predetermined mesh size;
 inverting the device so that the particles flow through the screening cup screens through which they will pass; and
 estimating or measuring the amount of particles retained on each screen.

7. The method of claim 6 wherein the screen sizes are checked for accuracy before use.

8. The method of claim 6 wherein there are screening cups having a screen sizes of 20, 30, 40, 50 and 70 mesh respectively.

9. The method of claim 6 wherein the measuring cup, the base cup and screening cup(s) of the device are made of material sufficiently transparent for particles to be seen through the walls or if opaque have viewing windows.

10. The method of claim 6 wherein the measuring cup, the base cup and screening cup(s) all have diameters less than about three inches and a height of less than about two inches.

* * * * *